US005614188A

United States Patent [19]
Urano et al.

[11] Patent Number: 5,614,188
[45] Date of Patent: Mar. 25, 1997

[54] ANTI-FUSARIUM COMPOSITION CONTAINING STRAINS OF BACILLUS SP., A CHITIN-CONTAINING MATERIAL, AND A POWDERY MATERIAL

[75] Inventors: Teruo Urano, Sano; Hiroshi Miyaji; Kazuhiro Maesato, both of Tokyo, all of Japan

[73] Assignee: Murakashi Lime Industry Co., Ltd., Tochigi Pref., Japan

[21] Appl. No.: 491,313

[22] Filed: Jun. 16, 1995

Related U.S. Application Data

[63] Continuation of Ser. No. 132,257, Oct. 6, 1993, abandoned.

[51] Int. Cl.⁶ .................... A01N 63/00; C12N 1/20
[52] U.S. Cl. ............... 424/93.46; 424/538; 435/252.5; 435/832
[58] Field of Search ..................... 424/93.46, 538; 435/252.5, 832

[56] References Cited

U.S. PATENT DOCUMENTS

| | | | |
|---|---|---|---|
| 4,477,433 | 10/1984 | Hultman | 424/93 Q |
| 4,489,161 | 12/1984 | Papvizas | 424/93 Q |
| 4,642,131 | 2/1987 | Hoitink | 424/93 Q |
| 4,647,537 | 3/1987 | Shigemitsu | 435/178 |
| 4,713,342 | 12/1987 | Chot et al. | 424/92 Q |
| 4,748,021 | 5/1988 | Chet et al. | 424/93 Q |
| 4,915,944 | 4/1990 | Chat et al. | 424/93 Q |
| 4,940,840 | 7/1990 | Suslow et al. | 800/205 |
| 5,041,290 | 8/1991 | Gindrat et al. | 424/93 Q |
| 5,049,379 | 9/1991 | Handelsman et al. | 424/115 |
| 5,215,747 | 6/1993 | Hairston et al. | 424/93 |
| 5,260,302 | 11/1993 | Fattori et al. | 424/93 Q |
| 5,270,039 | 12/1993 | You et al. | 424/93 Q |
| 5,344,647 | 9/1994 | Rossall | 424/93.462 |

Primary Examiner—Michael G. Wityshyn
Assistant Examiner—Kristin K. Larson
Attorney, Agent, or Firm—Cushman Darby & Cushman IP Group of Pillsbury Madison & Sutro LLP

[57] ABSTRACT

It is an object of the present invention to provide a soil-borne diseases controlling agent by the use of newly discovered microorganisms having strong antibacterial action. The soil-borne diseases controlling agent according to the present invention is characterized by that the agent comprises microorganisms selected from the group consisting of Bacillus sp. International Deposit Number FERM BP-4375 and Bacillus sp. International Deposit Number FERM BP-4376 as an active ingredient antagonistic against pathogenic Fusarium fungi (Fusarium species).

4 Claims, No Drawings

ANTI-FUSARIUM COMPOSITION CONTAINING STRAINS OF BACILLUS SP., A CHITIN-CONTAINING MATERIAL, AND A POWDERY MATERIAL

This is a continuation of application Ser. No. 08/132,257, filed on Oct. 6, 1993, now abandoned.

FIELD OF THE INVENTION

The present invention relates to a soil-borne diseases controlling agent antagonistic specifically against pathogenic Fusarium fungi.

DESCRIPTION OF THE PRIOR ART

Some kinds of microorganism in soil affect growth of plants and soil-borne diseases. The soil-borne diseases have being controlled by use of chemical agents, however, the controlling has problems of toxicity causing harmful effect on the human body and environment due to the residual chemicals in soil.

These days, the soil fertility of farm has been weakening by excessive application of agricultural chemicals and fertilizers, and troubles for continuous cropping on an identical farm are becoming more seriously. As a result, the farm management becomes more difficult due to decreasing product quality and productivity. About 60–70% of the continuous cropping trouble comes from soil-borne pathogenic microorganisms, however, only a few chemicals are effective in controlling the soil-borne diseases. Fumigants such as chloropicrin and methylbromide are commonly used for treating the soil contaminated by pathogenic microorganisms. Problems of the treatment is that fumigants destroy the ecosystem of microorganisms in soil due to the non-selective destruction with no consideration on their usefulness.

Accordingly, it is an object of the present invention to provide a novel soil-borne diseases controlling agent by the use of newly discovered microorganisms having strong antibacterial action.

SUMMARY OF THE INVENTION

The soil-borne diseases controlling agent according to the present invention is characterized by that the agent comprises microorganisms selected from the group consisting of International Deposit Number FERM BP-4375 and International Deposit Number FERM BP-4376 deposited in National Institute of Bioscience and Human-Technology (Agency of Industrial Science and Technology) of Japan as an active ingredient antagonistic against pathogenic Fusarium fungi (Fusarium species).

DETAILED DESCRIPTION OF THE PREFERRED EMBODIMENTS

FERM BP-4375 is a fungus deposited in the National Institute of Bioscience and Human-Technology of Japan under Deposit No. FERM P-12954 on May 14, 1992, and transferred to International deposit under Deposit No. FERM BP-4375 on Aug. 3, 1993, and has mycological property as shown in Table 1.

FERM BP-4376 is a fungus deposited in the National Institute of Bioscience and Human-Technology of Japan under Deposit No. FERM P-12955 on May 14, 1992, and transferred to International deposit under Deposit No. FERM BP-4376, and has mycological property as shown in Table 2.

TABLE 1

Mycological property of FERM BP-4375

| Mycological property | reaction |
|---|---|
| form | rod |
| Gram stain | positive |
| formation of spore | positive |
| reaction to oxygen | aerobic |
| colony in NA* culture medium | loose type |
| catalase activity | positive |
| production of ammonia | positive |
| hydrolysis of cottonseed oil | negative |
| hydrolysis of casein | positive |
| reaction of BCP* milk | alkali digestion |
| arginine | negative |
| glutamine | negative |
| lysine | negative |
| ornithine | negative |
| production of fluorochrome | negative |
| resistance at 80° C. | positive |
| Utility Test | |
| succinic acid | positive |
| fumaric acid | positive |
| malic acid | negative |
| pyruvic acid | positive |
| malonic acid | negative |
| benzoic acid | negative |
| formic acid | negative |
| itaconic acid | negative |
| hippuric acid | negative |
| tartaric acid | negative |
| pimeric acid | negative |
| triptamine | negative |
| mesaconic acid | negative |
| saccharinic acid | negative |
| fructose | negative |
| aesculin | negative |
| inuline | positive |
| sebacic acid | negative |
| heptanoic acid | negative |
| propionic acid | negative |
| adonite | negative |
| trehalose | positive |
| salicine | negative |
| melibiose | negative |
| sorbitol | negative |
| dulcitol | negative |
| cellobiose | negative |
| rhamnose | positive |
| inositol | positive |
| melezitose | negative |
| putrescine | negative |
| citric acid | negative |
| lactic acid | negative |
| betaine | negative |
| valine | negative |
| galactose | negative |
| erythrite | negative |
| citraconic acid | negative |
| threonine | negative |
| geraniol | negative |
| β-alanine | negative |
| suberic acid | negative |
| homoserine | negative |
| propylene glycol | negative |
| butanediol | negative |
| α-methyl-d-glucoside | negative |

NA*: Nutrient Agar
BCP*: Bromocresol Purple

TABLE 2

Mycological property of FERM BP-4376

| Mycological property | reaction |
| --- | --- |
| form | rod |
| Gram stain | positive |
| formation of spore | positive |
| reaction to oxygen | aerobic |
| colony in NA* culture medium | loose type |
| catalase activity | positive |
| production of ammonia | positive |
| reduction of nitrate | positive |
| liquefaction of gelatin | positive |
| production of $H_2S$ | positive |
| hydrolysis of starch | positive |
| hydrolysis of cottonseed oil | negative |
| hydrolysis of casein | positive |
| reaction of BCP* milk | alkali digestion |
| arginine | negative |
| glutamine | negative |
| lysine | negative |
| ornithine | negative |
| production of fluorochrome | negative |
| resistance at 80° C. | positive |
| Utility Test | |
| succinic acid | negative |
| fumaric acid | positive |
| malic acid | positive |
| pyruvic acid | positive |
| malonic acid | positive |
| benzoic acid | negative |
| formic acid | negative |
| itaconic acid | negative |
| hippuric acid | positive |
| tartaric acid | positive |
| pimeric acid | positive |
| triptamine | negative |
| mesaconic acid | positive |
| saccharinic acid | negative |
| sebacic acid | negative |
| heptanoic acid | negative |
| propionic acid | negative |
| adonite | positive |
| salicine | positive |
| melibiose | positive |
| sorbitol | positive |
| dulcitol | positive |
| cellobiose | positive |
| rhamnose | positive |
| inositol | positive |
| melezitose | positive |
| putrescine | negative |
| citric acid | negative |
| lactic acid | positive |
| betaine | positive |
| valine | positive |
| galactose | positive |
| citraconic acid | positive |
| threonine | positive |
| geraniol | negative |
| β-alanine | positive |
| suberic acid | positive |
| propylene glycol | positive |
| butanediol | positive |
| α-methyl-d-glucoside | positive |
| aesculin | positive |
| inuline | positive |

NA*: Nutrient Agar
BCP*: Bromocresol Purple

These fungi have antibacterial activity antagonistic against Fusarium species as indicated in the below-mentioned Example 1 (Table 3) and Example 2 (Table 4), and the activity is enhanced when one or both of them are combined with a material containing chitin. It is guessed that a certain antibiotic material is produced by nourishing FERM BP-4375 and/or FERM BP-4376 with chitin, and the produced antibiotic material inhibits growth of Fusarium species to result in the stimulation of the soil-borne diseases controlling activity.

The chitin-containing material usable for the present invention is not restricted specifically by the kind and grading in so far as the material contains chitin usually derived from shells of arthropod or mollusk. Preferred raw materials for the chitin-containing material are shells of crab or lobster due to the availability and easy processing.

The amount of FERM BP-4375 and/or FERM BP-4376 to be combined with the chitin-containing material is settled at about $1\times10^2$–$1\times10^9$ fungi/gram of chitin-containing material, preferably $1\times10^5$–$1\times10^7$ fungi/gram of chitin-containing material.

As to practical configurations of the present soil-borne diseases controlling agent, it is desirous from the standpoint of prolonged effectiveness, transportation, application, etc. that FERM BP-4375 and/or FERM BP-4376 combined with a chitin-containing material are further mixed with a powdery granular material. Otherwise, it is also helpful that FERM BP-4375 and/or FERM BP-4376 is carried on a powdery granular material first, and then a chitin-containing material is added thereto.

As to the mixing ratio of the powdery granular material and the chitin-containing material for a mixture composition in which FERM BP-4375 and/or FERM BP-4376 are contained, it is preferable that the resulting mixture have a pH value of 7.0–9.5. Thus pH-adjusted composition can maintain the activity of fungi for a longer period of time.

The powdery granular material mixed for adjusting pH values is exemplified by crushed limestone, crushed dolomite, crushed magnesite and crushed light-weight aerated concrete (ALC). Though the kind and grading of the material are not restricted specifically, it is desirous to use porous ones having high water absorption and acidity regulating activity.

Instead of mixing the fungi-bearing chitin-containing material with a powdery granular material, a predetermined number of fungi may be carried on the powdery granular material, and then a chitin-containing material may be added thereto.

When the powdery granular material is limestone, soft-porous limestone formed after the Cainozoic era by calcification in shallow sea under no affection of metamorphose is preferred to dense-crystalline limestone formed before the Mesozoic era because of better settling of the microorganism and better performance as a carrier. Such a soft-porous limestone was formed in the Miocene era (20–30 million years ago) and is mainly obtainable in the South East Asia area. Crushed light-weight aerated concrete is a hydrated calcium silicate ($CaO.SiO_2.nH_2O$) containing tobermorite as the principal component. Air is introduced when the concrete is formed, and is mainly used as construction materials. The concrete is employed in the present invention in a crushed form of smaller than 5 mm. Further, granules and powders of calcium carbonate and magnesium carbonate are also used as carriers of the microorganisms.

By the application to soil of the present soil-borne diseases controlling agent containing the antibacterial microorganisms as an active ingredient, controlling of phytopathosis caused by pathogenic Fusarium species is achieved as the effect. The present invention will be explained in detail by reference of Examples, however, the invention never be limited by the Examples.

EXAMPLE 1

Into each petri dish was dispensed 20 ml (milliliter) of a culture medium of TRIPTIC SOY BROTH (®; produce of DIFCO Co.) containing 1.0 wt % of agar. A test strain FERM BP-4375 and an indication strain Fusarium species were seeded on the same culture medium, and a dual culture under dark conditions was conducted for a period of from 24 to 240 hours. The antibacterial activity of the test strain was evaluated by reference to the growth inhibitory belt formed between the test stain and the indication strain. The result is shown in Table 3. As clearly understandable from the Table, FERM BP-4375 is noticed to be active or strongly active in controlling the Fusarium species.

TABLE 3

(Antibacterial Activity of FERM BP-4375)

| Pathogenic fungus | Activity evaluated |
|---|---|
| Fusarium oxysporum f. sp. lagenariae | +++ |
| Fusarium oxysporum f. sp. lycopersici | +++ |
| Fusarium oxysporum f. sp. cucumerinum | ++ |
| Fusarium oxysporum f. sp. niveum | +++ |
| Fusarium oxysporum f. sp. raphani | ++ |
| Fusarium oxysporum f. sp. allii | +++ |
| Fusarium oxysporum f. sp. cepae | +++ |
| Fusarium oxysporum f. sp. batatas | +++ |
| Fusarium oxysporum f. sp. asparagi | +++ |
| Fusarium oxysporum f. sp. spinaciae | ++ |
| Fusarium oxysporum f. sp. fragariae | +++ |
| Fusarium oxysporum f. sp. melongenae | ++ |
| Fusarium oxysporum f. sp. garlic | +++ |
| Fusarium oxysporum f. sp. cucurbitae | +++ |
| Fusarium oxysporum f. sp. arctii | +++ |
| Fusarium oxysporum f. sp. melonis | +++ |
| Fusarium oxysporum f. sp. phaseoli | +++ |
| Fusarium oxysporum f. sp. lactucae | ++ |
| Fusarium oxysporum f. sp. cerealis | ++ |
| Fusarium arthrosporioides | +++ |
| Fusarium oxysporum f. sp. fabae | +++ |
| Fusarium oxysporum f. sp. conglutinans | +++ |
| Fusarium solani | ++ |

+ + +: strongly active
+ +: active
+: weakly active

EXAMPLE 2

Into each petri dish was dispensed 20 ml of a culture medium of TRIPTIC SOY BROTH (®; produce of DIFCO Co.) containing 1.0 wt % of agar. A test strain FERM BP-4376 and an indication strain Fusarium species were seeded on the same culture medium, and a dual culture under dark conditions was conducted for a period of from 24 to 240 hours.

TABLE 4

(Antibacterial Activity of FERM BP-4376)

| Pathogenic fungus | Activity evaluated |
|---|---|
| Fusarium oxysporum f. sp. lagenariae | ++ |
| Fusarium oxysporum f. sp. lycopersici | +++ |
| Fusarium oxysporum f. sp. cucumerinum | ++ |
| Fusarium oxysporum f. sp. niveum | ++ |
| Fusarium oxysporum f. sp. raphani | ++ |
| Fusarium oxysporum f. sp. allii | +++ |
| Fusarium oxysporum f. sp. cepae | ++ |
| Fusarium oxysporum f. sp. batatas | ++ |
| Fusarium oxysporum f. sp. asparagi | +++ |
| Fusarium oxysporum f. sp. spinaciae | +++ |
| Fusarium oxysporum f. sp. fragariae | ++ |
| Fusarium oxysporum f. sp. melongenae | ++ |
| Fusarium oxysporum f. sp. garlic | +++ |
| Fusarium oxysporum f. sp. cucurbitae | ++ |
| Fusarium oxysporum f. sp. arctii | +++ |
| Fusarium oxysporum f. sp. melonis | ++ |

TABLE 4-continued (Antibacterial Activity of FERM BP-4376)

| Pathogenic fungus | Activity evaluated |
|---|---|
| Fusarium oxysporum f. sp. phaseoli | +++ |
| Fusarium oxysporum f. sp. lactucae | +++ |
| Fusarium oxysporum f. sp. cerealis | +++ |
| Fusarium arthrosporioides | +++ |
| Fusarium oxysporum f. sp. fabae | ++ |
| Fusarium oxysporum f. sp. conglutinans | ++ |
| Fusarium solani | ++ |

+ + +: strongly active
+ +: active
+: weakly active

The antibacterial activity of the test strain was evaluated by reference to the growth inhibitory belt formed between the test stain and the indication strain. The result is shown in Table 4. As clearly understandable from the Table, FERM BP-4376 is noticed to be active or strongly active in controlling the Fusarium species.

EXAMPLE 3

FERM BP-4375 was cultivated in a shaker for 168 hours under shaking of 160 rpm rotation, in which was used a liquid culture medium containing 0.2 wt % of yeast extract and 0.5 wt % of peptone being adjusted at pH 7.0. The resulting culture medium containing $1 \times 10^9$ FERM BP-4375 fungi/ml medium was mixed with a crab shell derived chitin of smaller than 5 mm, thereby a soil-borne diseases controlling agent containing $2 \times 10^7$ FERM BP-4375 fungi/g chitin was obtained. A 1/2000a (are; 100m$^2$) Wagner pot was filled with steam-sterilized ando soil (andosol) and fertilized with 1.3 g of N, 1.0 g of $P_2O_5$, 1.0 g of $K_2O$ and 1.0 /g of CaO. To the pot was applied 1.25 g/pot of the above-mentioned controlling agent.

EXAMPLE 4

To a 1/2000a Wagner pot filled with ando soil being prepared in the same manner as Example 3 was applied the cultivated FERM BP-4375 of a number of fungi corresponding to that of fungi in Example 3.

Comparative Example 1

To a 1/2000a Wagner pot filled with ando soil being prepared in the same manner as Example 3 was applied the crab shell derived chitin of smaller than 5 mm of the same amount corresponding to the amount in Example 3.

Comparative Example 2

A 1/2000a Wagner pot filled with ando soil being prepared in the same manner as Example 3 was utilized for the test. No additive other than the fertilizer was used.

To respective pots for Examples 3, 4, Comparative Examples 1 and 2 were added $1 \times 10^2$ fungi/g soil of Fusarium oxysporum f. sp. lycopersici as a pathogenic fungus. Ten tomato seedlings of the first fruit cluster blooming stage were planted per lot, and no further fertilizer was applied. The control effect upon the phytopathosis at 50 days after the plantation was observed, and the result is shown in Table 5. The percentage of infected seedlings obtained by Example 4 in which FERM BP-4375 was applied as itself is smaller by comparison with that for Comparative Example 2 of no fungal application or for Comparative Example 1 of chitin application only. A remarkable reduction in the percentage of infected seedlings is noticed for Example 3 in which FERM BP-4375 was applied in combination with crab shell derived chitin.

TABLE 5

| Pot for plantation test | Percentage of infected seedling* |
|---|---|
| Example 3 | 40 |
| Example 4 | 60 |
| Comparative Example 1 | 80 |
| Comparative Example 2 | 100 |

* $\frac{\text{number of infected seedlings}}{10} \times 100\%$

EXAMPLE 5

FERM BP-4376 cultivated in the same manner as Example 3 was added to a crab shell derived chitin of smaller than 5 mm thereby was prepared a soil-borne diseases controlling agent containing $2 \times 10^7$ FERM BP-4376 fungi/g chitin. To a 1/2000a Wagner pot prepared in the same manner as Example 3 was applied 1.25 g/pot of the above-mentioned controlling agent.

EXAMPLE 6

To a 1/2000a Wagner pot filled with ando soil being prepared in the same manner as Example 3 was applied cultivated FERM BP-4376 corresponding in number to that of Example 5.

Comparative Example 3

To a 1/2000a Wagner pot filled with ando soil being prepared in the same manner as Example 3 was applied a crab shell derived chitin of smaller than 5 mm corresponding in amount to that of Example 5.

Comparative Example 4

A 1/2000a Wagner pot filled with ando soil being prepared in the same manner as Example 3 was utilized for the test. No additive other than the fertilizer was used.

To respective pots for Examples 5, 6, Comparative Examples 3 and 4 were added $1 \times 10^2$ fungi/g soil of *Fusarium oxysporum f. sp. lycopersici* as a pathogenic fungus. Ten tomato seedlings of the first fruit cluster blooming stage were planted per lot, and no further fertilizer was applied. The control effect upon the phytopathosis at 50 days after the plantation was observed, and the result is shown in Table 6. The percentage of infected seedlings obtained by Example 4 in which FERM BP-4376 was applied as itself is smaller by comparison with that for Comparative Example 4 of no fungal application or for Comparative Example 3 of chitin application only. A remarkable reduction in the percentage of infected seedlings is noticed for Example 5 in which FERM BP-4376 was applied in combination with crab shell derived chitin.

TABLE 6

| Pot for plantation test | Percentage of infected seedling* |
|---|---|
| Example 5 | 50 |
| Example 6 | 70 |
| Comparative Example 3 | 80 |
| Comparative Example 4 | 100 |

* $\frac{\text{number of infected seedlings}}{10} \times 100\%$

EXAMPLE 7

FERM BP-4375 cultivated in the same manner as Example 3 was added to a crab shell derived chitin of smaller than 5 mm to prepare a composition containing $2 \times 10^7$ FERM BP-4375 fungi/g chitin, and the composition was added to KUZUU-limestone (dolomite) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 8

FERM BP-4375 cultivated in the same manner as Example 3 was added to a crab shell derived chitin of smaller than 5 mm to prepare a composition containing $2 \times 10^7$ FERM BP-4375 fungi/g chitin, and the composition was added to OKINAWA-limestone (coral) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 9

FERM BP-4375 cultivated in the same manner as Example 3 was added to a crab shell derived chitin of smaller than 5 mm to prepare a composition containing $2 \times 10^7$ FERM BP-4375 fungi/g chitin, and the composition was added to INDONESIAN-limestone (the Miocene era; soft and porous limestone) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 10

FERM BP-4375 cultivated in the same manner as Example 3 was added to a crab shell derived chitin to prepare a soil-borne diseases controlling agent containing $2 \times 10^7$ FERM BP-4375 fungi/g chitin. To a 1/2000a Wagner pot prepared in the same manner as Example 3 was applied 1.25 g/pot of the above-mentioned controlling agent.

Comparative Example 5

To a 1/2000a Wagner pot filled with ando soil being prepared in the same manner as Example 3 was added the same amount of KUZUU-limestone in Example 7.

Comparative Example 6

To a 1/2000a Wagner pot filled with ando soil being prepared in the same manner as Example 3 was added OKINAWA-limestone of the same amount as in Example 8.

Comparative Example 7

To a 1/2000a Wagner pot filled with ando soil being prepared in the same manner as Example 3 was added INDONESIAN-limestone (the Miocene era; soft and porous limestone) of the same amount as in Example 9.

Comparative Example 8

A 1/2000a Wagner pot filled with ando soil being prepared in the same manner as Example 3 was utilized for the test. No additive other than the fertilizer was used.

To respective pots for Examples 7–10 and Comparative Examples 5–8 were added 1×10² fungi/g soil of *Fusarium oxysporum f.* sp. *lycopersici* as a pathogenic fungus. Ten tomato seedlings of the first fruit cluster blooming stage were planted per lot, and no further fertilizer was applied. The control effect upon the phytopathosis at 50 days after the plantation was observed, and the result is shown in Table 7. The percentage of infected seedlings obtained by Examples 7, 8 and 9 in which FERM BP-4375 was applied as a composition comprising the strain added chitin derived from crab shell and powdery granular material is smaller than that by Example 10 in which FERM BP-4375 was applied in combination only with crab shell derived chitin. It is clear from the result obtained by Comparative Examples 5–7 that the reduction is not resulted from the effect of the powdery granular material itself.

TABLE 7

| Pot for plantation test | Percentage of infected seedling* |
| --- | --- |
| Example 7 | 20 |
| Example 8 | 20 |
| Example 9 | 10 |
| Example 10 | 40 |
| Comparative Example 5 | 90 |
| Comparative Example 6 | 100 |
| Comparative Example 7 | 90 |
| Comparative Example 8 | 100 |

* $\frac{\text{number of infected seedlings}}{10} \times 100\%$

EXAMPLE 11

FERM BP-4376 cultivated in the same manner as Example 5 was added to a crab shell derived chitin of smaller than 5 mm to prepare a composition containing 2×10⁷ FERM BP-4376 fungi/g chitin, and the composition was added to KUZUU-limestone (dolomite) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 12

FERM BP-4376 cultivated in the same manner as Example 5 was added to a crab shell derived chitin of smaller than 5 mm to prepare a composition containing 2×10⁷ FERM BP-4376 fungi/g chitin, and the composition was added to OKINAWA-limestone (coral) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 13

FERM BP-4376 cultivated in the same manner as Example 5 was added to a crab shell derived chitin of smaller than 5 mm to prepare a composition containing 2×10⁷ FERM BP-4376 fungi/g chitin, and the composition was added to INDONESIAN-limestone (the Miocene era; soft and porous limestone) to obtain a soil-borne diseases controlling agent containing 5 wt % of the composition. To a 1/2000a Wagner pot prepared in the same manner as Example 3 was applied 25 g/pot of the above-mentioned controlling agent.

EXAMPLE 14

FERM BP-4376 cultivated in the same manner as Example 5 was added to a crab shell derived chitin to prepare a soil-borne diseases controlling agent containing 2×10⁷ FERM BP-4376 fungi/g chitin. To a 1/2000a Wagner pot prepared in the same manner as Example 3 was applied 1.25 g/pot of the above-mentioned controlling agent.

Comparative Example 9

To a 1/2000a Wagner pot filled with ando soil being prepared in the same manner as Example 3 was added KUZUU-limestone of the same amount as in Example 11.

Comparative Example 10

To a 1/2000a Wagner pot filled with ando soil being prepared in the same manner as Example 3 was added OKINAWA-limestone of the same amount as in Example 12.

Comparative Example 11

To a 1/2000a Wagner pot filled with ando soil being prepared in the same manner as Example 3 was added INDONESIAN-limestone (the Miocene era; soft and porous limestone) of the same amount as in Example 9.

Comparative Example 12

A 1/2000a Wagner pot filled with ando soil being prepared in the same manner as Example 3 was utilized for the test.

To respective pots for Examples 11–14 and Comparative Examples 9–12 were added 1×10² fungi/g soil of *Fusarium oxysporum f.* sp. *lycopersici* as a pathogenic fungus. Ten tomato seedlings of the first fruit cluster blooming stage were planted per lot, and no further fertilizer was applied. The control effect upon the phytopathosis at 50 days after the plantation was observed, and the result is shown in Table 8. The percentage of infected seedlings obtained by Examples 11, 12 and 13 in which FERM BP-4376 was applied as a composition comprising the strain added chitin derived from crab shell and powdery granular material is smaller than that by Example 14 in which FERM BP-4376 was applied in combination only with crab shell derived chitin. It is clear from the result obtained by Comparative Examples 9–11 that the reduction is not resulted from the effect of the powdery granular material itself.

TABLE 8

| Pot for plantation test | Percentage of infected seedling* |
| --- | --- |
| Example 11 | 30 |
| Example 12 | 30 |
| Example 13 | 20 |
| Example 14 | 50 |
| Comparative Example 9 | 90 |
| Comparative Example 10 | 100 |
| Comparative Example 11 | 90 |
| Comparative Example 12 | 100 |

* $\frac{\text{number of infected seedlings}}{10} \times 100(\%)$

The soil-borne diseases controlling agent according to the present invention is capable of controlling effectively phytopathosis caused by pathogenic Fusarium fungi without resulting in harmful effect on the human body and environment.

We claim:

1. An antifungal composition for controlling Fusarium comprising an anti-fusarium effective amount of microorganisms selected from the group consisting of Bacillus sp. FERM BP-4375 and Bacillus sp. FERM BP-4376, a chitin-containing material obtained from antropod or mollusk shells pod and powdery material selected from the group consisting of crushed limestone and crushed dolomite.

2. A biologically pure culture of Bacillus sp. FERM BP-4375.

3. A biologically pure culture of Bacillus sp. FERM BP-4376.

4. A method of controlling. Fusarium fungi in soil which comprises applying to soil in need of such treatment an anti-Fusarium effective amount of a composition comprising microorganisms selected from the group consisting of Bacillus sp. FERM BP-4375 and Bacillus sp. FERM BP-4376, a chitin-containing material obtained from arthropod or mollusk shells and a powdery granular material selected from the group consisting of crushed limestone and crushed dolomite.

* * * * *